United States Patent

Kishita et al.

Patent Number: 4,898,958
Date of Patent: Feb. 6, 1990

[54] ORGANOSILICON COMPOUND

[75] Inventors: Hirofumi Kishita, Annaka; Koichi Yamaguchi, Takasaki; Akira Yoshida, Tokyo, all of Japan

[73] Assignee: Shin-Etsu Chemical Co., Ltd., Tokyo, Japan

[21] Appl. No.: 242,173

[22] Filed: Sep. 9, 1988

[30] Foreign Application Priority Data

Sep. 11, 1987 [JP] Japan .................................. 62-227909

[51] Int. Cl.⁴ .............................................. C07F 7/08
[52] U.S. Cl. ..................................................... 556/448
[58] Field of Search ......................................... 556/448

[56] References Cited

U.S. PATENT DOCUMENTS

| | | | |
|---|---|---|---|
| 2,934,515 | 4/1960 | Konkles et al. | 556/448 X |
| 2,979,519 | 4/1961 | Pierce et al. | 556/448 |
| 3,070,617 | 12/1962 | Holbrook | 556/448 |
| 3,422,131 | 1/1969 | Pittman et al. | 556/448 |
| 3,423,234 | 1/1969 | Heine | 556/448 X |
| 3,529,003 | 9/1970 | Rausch et al. | 556/448 |
| 3,575,921 | 4/1971 | Lee | 516/448 X |
| 3,639,156 | 1/1972 | Pittman et al. | 556/448 X |
| 3,876,677 | 4/1975 | Wu | 556/448 |

Primary Examiner—Paul F. Shaver
Attorney, Agent, or Firm—Oblon, Spivak, McClelland, Maier & Neustadt

[57] ABSTRACT

An organosilicon compound represented by general formula (I):

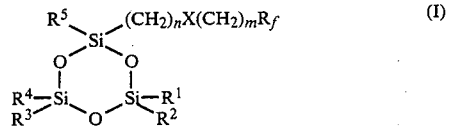

wherein $R^1$, $R^2$, $R^3$, $R^4$ and $R^5$ may be the same or different and each represent an alkyl group having 1 to 4 carbon atoms; $R_f$ represents $-C_lF_{2l+1}$ where l represents an integer of 3 to 10,

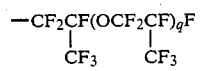

where q represents an integer of 1 to 5, or

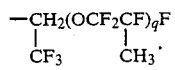

where q is as defined above; and X represents —O— or —CH₂—; provided that n is 3 and m is an integer of 0 to 2 when X represents —O—, and n is 0 and m is 1 when X represents —CH₂—. The compound is useful for preparing silicone polymers having a high thermal resistance, chemical resistance and weathering resistance and have a small surface energy.

2 Claims, 9 Drawing Sheets

ORGANOSILICON COMPOUND

BACKGROUND OF THE INVENTION

1. Field of the Invention

This invention relates to a novel organosilicon compound, and, more particularly, it is concerned with an organosilicon compound useful as a raw material for silicone oils or elastomers that have a high thermal resistance, chemical resistance and weathering resistance and have a small surface energy.

2. Description of Prior Art

Hitherto known as fluorine-containing cyclotrisiloxane is the one represented by the formula:

$$\begin{array}{c} CH_3 \\ \diagdown \\ CH_3 \end{array} Si \begin{array}{c} O \\ \diagup \\ O \end{array} Si \begin{array}{c} CH_3 \\ \diagup \\ (CH_2)_2-CF_3 \end{array} \quad \text{or}$$
$$\begin{array}{c} CH_3 \diagdown \\ CH_3 \diagup \end{array} Si \begin{array}{c} \\ \\ \end{array}$$

$$\begin{array}{c} CH_3 \\ \diagdown \\ CH_3 \end{array} Si \begin{array}{c} O \\ \diagup \\ O \end{array} Si \begin{array}{c} CH_3 \\ \diagup \\ (CH_2)_2-CF_3 \end{array}$$
$$\begin{array}{c} CH_3 \diagdown \\ (CH_2)_2-CF_3 \diagup \end{array} Si$$

(I. P. Yudina et al, Gazov. Khromatogr., No. 3, 120 (1965))

The organosilicon compound this invention provides is a substance that has been hitherto unknown.

SUMMARY OF THE INVENTION

An object of this invention is to provide a novel organosilicon compound useful as a raw material for silicone oils or elastomers that have a high thermal resistance, chemical resistance and weathering resistance and have a small surface energy.

According to this inventon, there is provided an organosilicon compound represented by general formula (I):

$$\begin{array}{c} R^5 \\ \diagdown \\ O \end{array} Si \begin{array}{c} (CH_2)_nX(CH_2)_mR_f \\ \diagup \\ O \end{array} \quad (I)$$
$$\begin{array}{c} R^4-Si \\ R^3 \diagup \end{array} \begin{array}{c} \\ O \end{array} \begin{array}{c} Si-R^1 \\ R^2 \end{array}$$

wherein $R^1$, $R^2$, $R^3$, $R^4$ and $R^5$ may be the same or different and each represent an alkyl group having 1 to 4 carbon atoms; $R_f$ represents $-C_lF_{2l+1}$ where l represents an integer of 3 to 10, $$\begin{array}{c} -CF_2CF(OCF_2CF)_qF \\ | \quad\quad\quad | \\ CF_3 \quad\quad CF_3 \end{array}$$

where q represents an integer of 1 to 5, or $$\begin{array}{c} -CH_2(OCF_2CF)_qF \\ | \quad\quad\quad | \\ CF_3 \quad\quad CH_3 \end{array}$$

where q is as defined above; and X represents $-O-$ or $-CH_2-$; provided that n is 3 and m is an integer of 0 to 2 when X represents $-O-$, and n is 0 and m is 1 when X represents $-CH_2-$.

The organosilicon compound of this invention is a novel compound useful, for example, as a raw material for silicone oils or elastomers that have a high thermal resistance, chemical resistance and weathering resistance and have a small surface energy.

DETAILED DESCRIPTION OF PREFERRED EMBODIMENTS OF THE INVENTION

Figure 1:
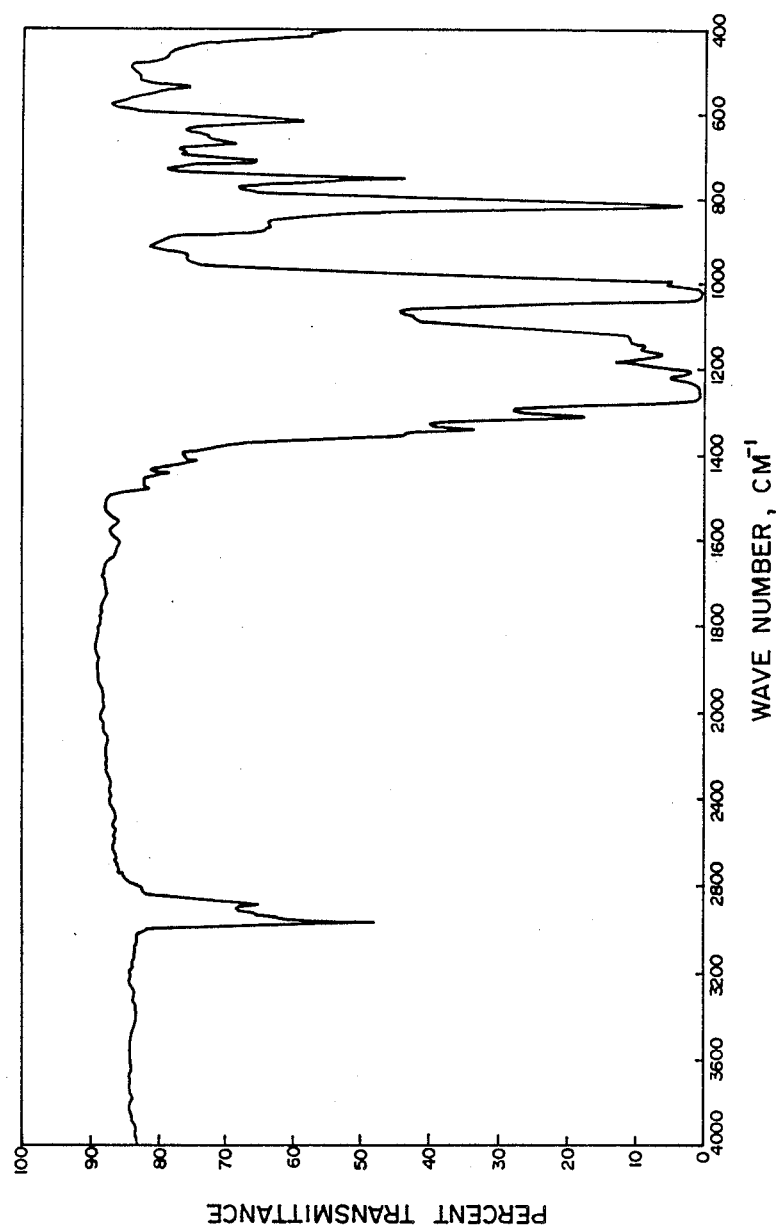
FIGS. 1 to 9 show IR spectra of organic compounds of this invention, obtained in Examples 1 to 9, respectively.

In the organosilicon compound of this invention, the groups $R^1$, $R^2$, $R^3$, $R^4$ and $R^5$ in general formula (I) may be the same or different and each represent an alkyl group having 1 to 4 carbon atoms, as exemplified by a methyl group, an ethyl group, a propyl group, a isopropyl group and a butyl group.

The group $R_f$ and/or X may be appropriately selected, so that the above properties of the silicone oils or elastomers obtained by using said compound as a raw material can be changed depending on their uses.

The organosilicon compound of this invention can be synthesized, for example, by reacting a disiloxanediol represented by general formula (II):

$$\begin{array}{c} R^4 \quad\quad R^1 \\ | \quad\quad\quad | \\ HO-Si-O-Si-OH \\ | \quad\quad\quad | \\ R^3 \quad\quad R^2 \end{array} \quad (II)$$

wherein $R^1$, $R^2$, $R^3$ and $R^4$ are as defined above: with a dichlorosilane compound having a fluorine-containing group, represented by general formula (III):

$$\begin{array}{c} R^5 \\ | \\ Cl_2-Si-(CH_2)_nX(CH_2)_mR_f \end{array} \quad (III)$$

wherein $R^5$, $R_f$, X, m and n are as defined above; in the presence of a catalyst. Useful as the catalyst in this reaction are, for example, amines such as triethylamine, pyridine, dimethylaniline, diethylamine and urea, and it may preferably be added in an amount of from 1 to 6 mol, particularly from 2 to 3 mol, per mol of the dichlorosilane compound. The reaction may preferably be carried out at a temperature of from 0° to 100° C., particularly from 30° to 70° C.

The above reaction can be carried out, for example, by separately preparing the respective solutions of the compounds of the above general formulas (II) and (III), and adding these in a solution containing the catalyst.

Preferred as solvents for the disiloxanediol represented by the above general formula (II) are polar solvents such as methyl ethyl ketone, acetone and ethyl acetate, and preferred as solvents for the dichlorosilane compound represented by the above general formula (III) are fluorinated hydrocarbon solvents such as m-xylene hexafluoride, perfluorooctane and 1,1,2-trichlorotrifluoroethane.

The thus obtained organosilicon compound of this invention, represented by general formula (I) is useful as a raw material for silicone oils or elastomers. Allowing this organosilicon compound to react, for example, in the presence of an alkaline catalyst such as KOH or $(n-C_4H_9)_4POH$ or an acidic catalyst such as $H_2SO_4$ or $CF_3S_3H$ may readily effect ring-opening polymerization through the same equilibration as in the case of hexamethylcyclotrisiloxane conventionally known, to produce a linear siloxane polymer. The resulting linear siloxane polymer is useful as a raw material for all sorts of silicone oils or elastomers. In particular, the organosilicon compound of this invention, which contains many fluorine atoms in the molecule, can make higher the thermal resistance, chemical resistance and weathering resistance of the siloxane polymer obtained by polymerization, and also can produce polymers having smaller surface energy and, therefore, having higher levels also in respect of water repellency, oil repellency and release properties than the conventional siloxane polymers do.

This invention will be described below in greater detail by giving Examples, but this invention is by no means limited to these.

EXAMPLES

Example 1

In four-necked flask having an internal volume of 2 lit., 600 ml of m-xylene hexafluoride was placed, and 53 g of triethylamine was dissolved therein. Fitted to this flask were two 500 ml dropping funnels, and placed in one of the dropping funnels was a solution of 156 g of dichlorosilane having a fluorine-containing group, represented by formula (IV):

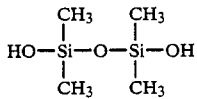  (IV)

in 150 ml of m-xylene hexafluoride, and placed in the other dropping funnels was a solution of 44.8 g of disiloxanediol represented by the formula:

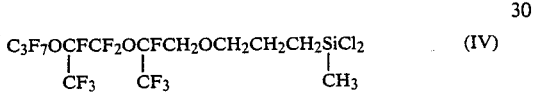

in 150 ml of methyl ethyl ketone. After the temperature of the triethylamine solution in the flask was raised to 50° C., the dichlorosilane solution and the disiloxanediol solution were dropwise added thereto from the two dropping funnels, respectively, at substantially the same dropping rate (about 1 ml/min) to carry out reaction. After completion of addition, the reaction mixture was stirred for 30 minutes. The resulting reaction product was washed with water to remove the by-product triethylamine hydrochloride, and then the organic layer thus obtained was separated and distilled under reduced pressure to yield 149.6 g of a compound as a fraction of 121° C./4 mmHg.

The compound thus obtained was subjected to elemental analysis and also to measurement of IR spectrum and NMR spectrum to obtain the following results.

Elemental anaylsis: (%)

|  | C | H | Si | F |
|---|---|---|---|---|
| Calculated*(%): | 27.95 | 3.17 | 11.53 | 44.21 |
| Found (%): | 27.93 | 3.15 | 11.55 | 44.23 |

(*as $C_{17}H_{23}O_6F_{17}Si_3$)

IR spectrum: As shown in FIG. 1.

Characteristic absorption (cm$^{-1}$): 1,020 (Si—O), 1,000–1,400 (C—F).

NMR spectrum: δ(ppm) (in CCl$_4$; internal standard: CHCl$_3$)
0.40–0.73 (m, 2H, Si—CH$_2$—C),
1.37–1.93 (m, 2H, C—CH$_2$—C),
3.37–3.67 (t, 2H, C—CH$_2$—O),
3.77–4.10 (d, 2H, O—CH$_2$—CF).

From the above results, the compound obtained was confirmed to be an organosilicon compound represented by the formula:

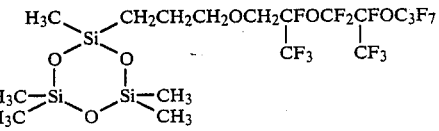

Yield: 82%.

Example 2

In four-necked flask having an internal volume of 2 lit., 500 ml of m-xylene hexafluoride was placed, and 41.4 g of triethylamine was dissolvd therein. Fitted to this flask were two 300 ml dropping funnels, and placed in one of the dropping funnels was a solution of 122.2 g of dichlorosilane having a fluorine-containing group, represented by formula (V):

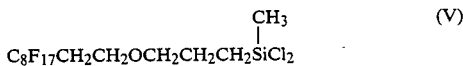  (V)

in 100 ml of m-xylene hexafluoride, and placed in the other dropping funnels was a solution of 34.9 g of the same disiloxanediol as used in Example 1 in 150 ml of methyl ethyl ketone. After the temperature of the triethylamine solution in the flask was raised to 50° C., the dichlorosilane solution and the disiloxanediol solution were dropwise added thereto from the two dropping funnels, respectively, at substantially the same dropping rate (about 1 ml/min) to carry out reaction. After completion of addition, the reaction mixture was stirred for 30 minutes. The resulting reaction product was washed with water to remove the by-product triethylamine hydrochloride, and the organic layer thus obtained was separated and distilled under reduced pressure to yield 464.3 g of a compound as a fraction of 134° C./3 mmHg.

Next, the thus obtained compound was subjected to elemental analysis and also to measurement of IR spectrum and NMR spectrum to obtain the following results. Elemental analysis: (%)

|  | C | H | Si | F |
|---|---|---|---|---|
| Calculated*(%): | 30.34 | 3.54 | 11.82 | 45.32 |
| Found (%): | 30.36 | 3.53 | 11.80 | 45.34 |

(*as $C_{18}H_{25}O_4F_{17}Si_3$)

Figure 2:
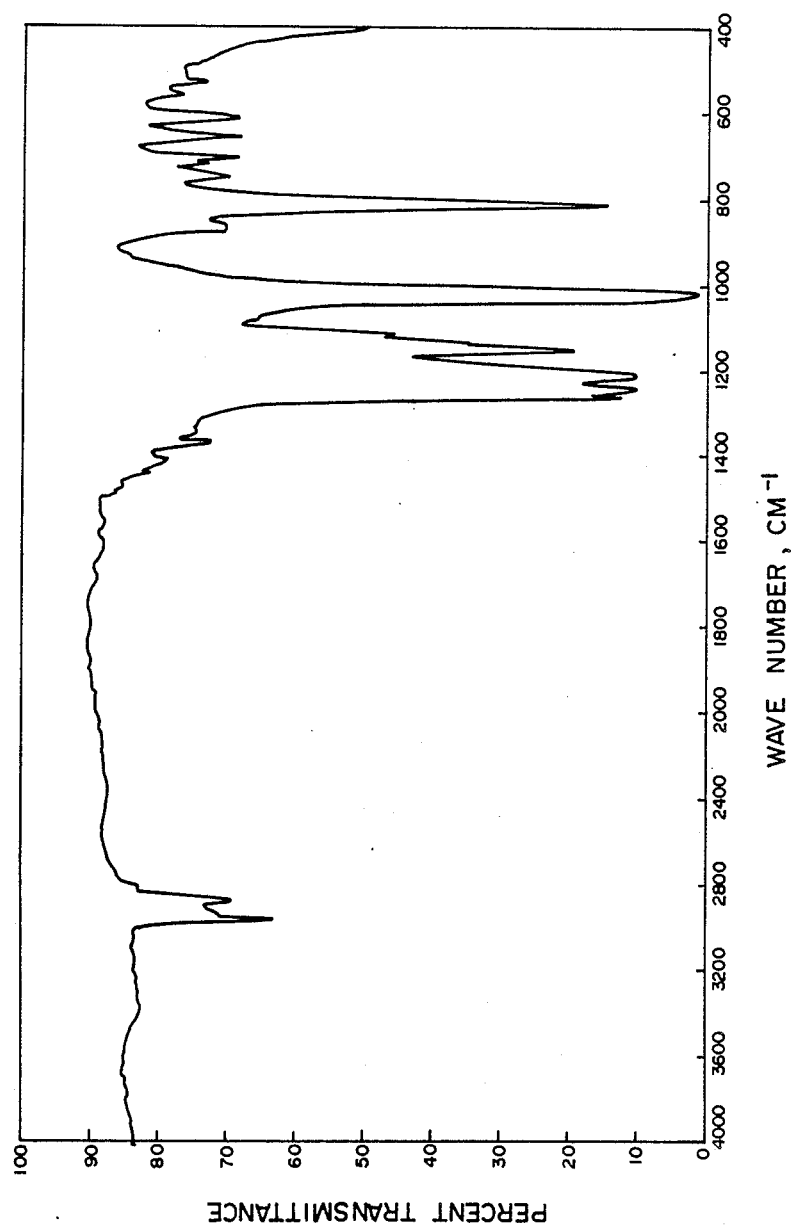
Figure 3:
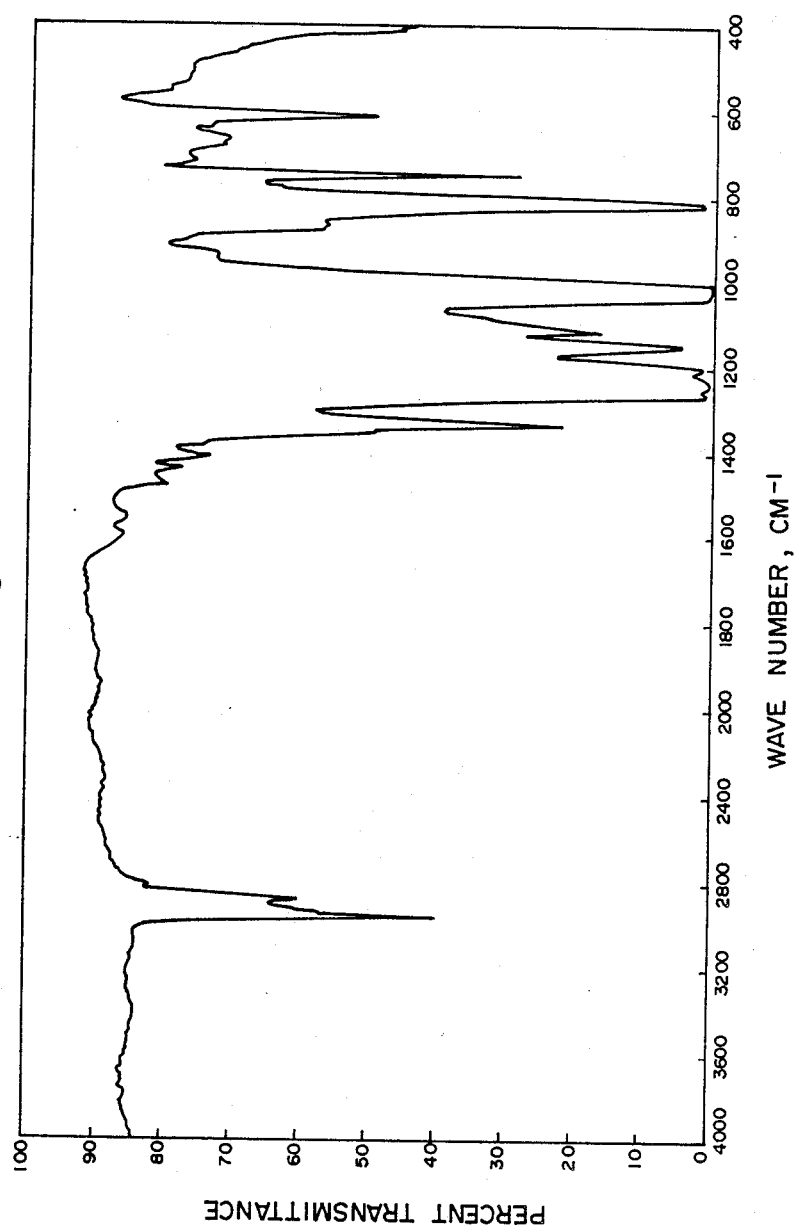
Figure 4:
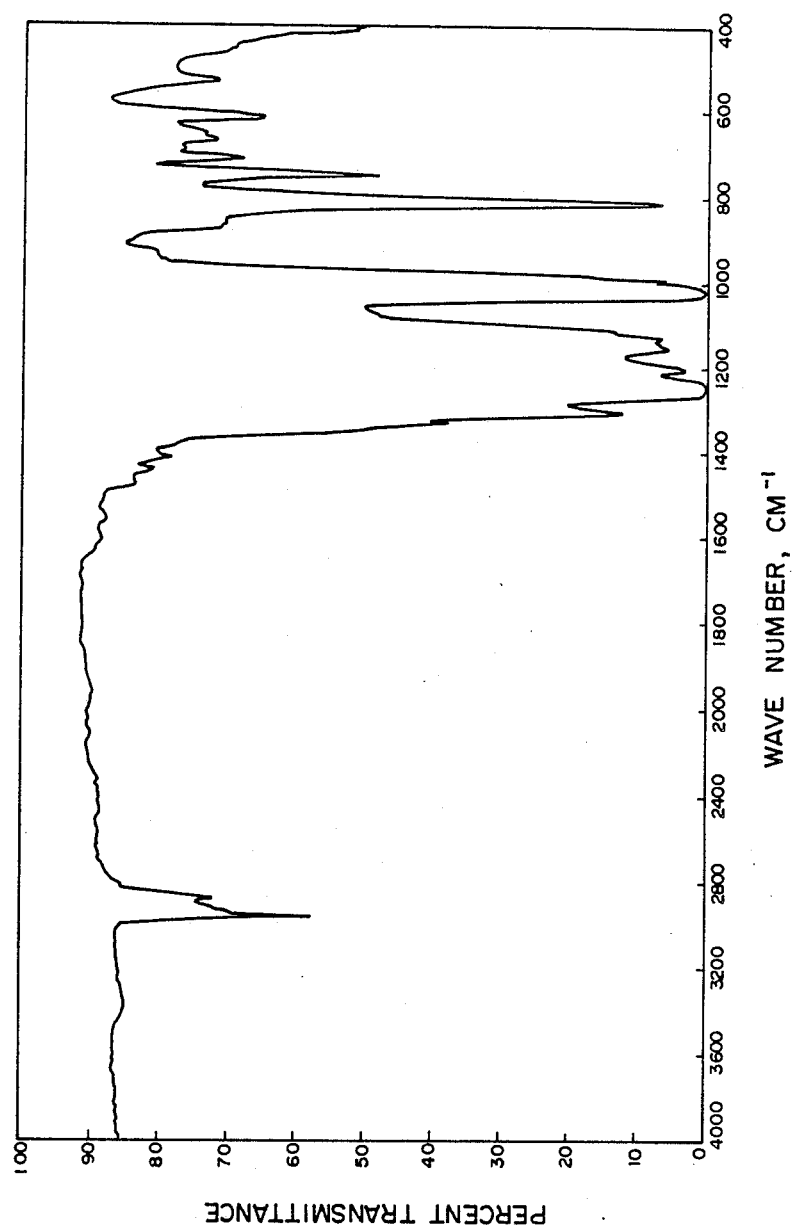
Figure 5:
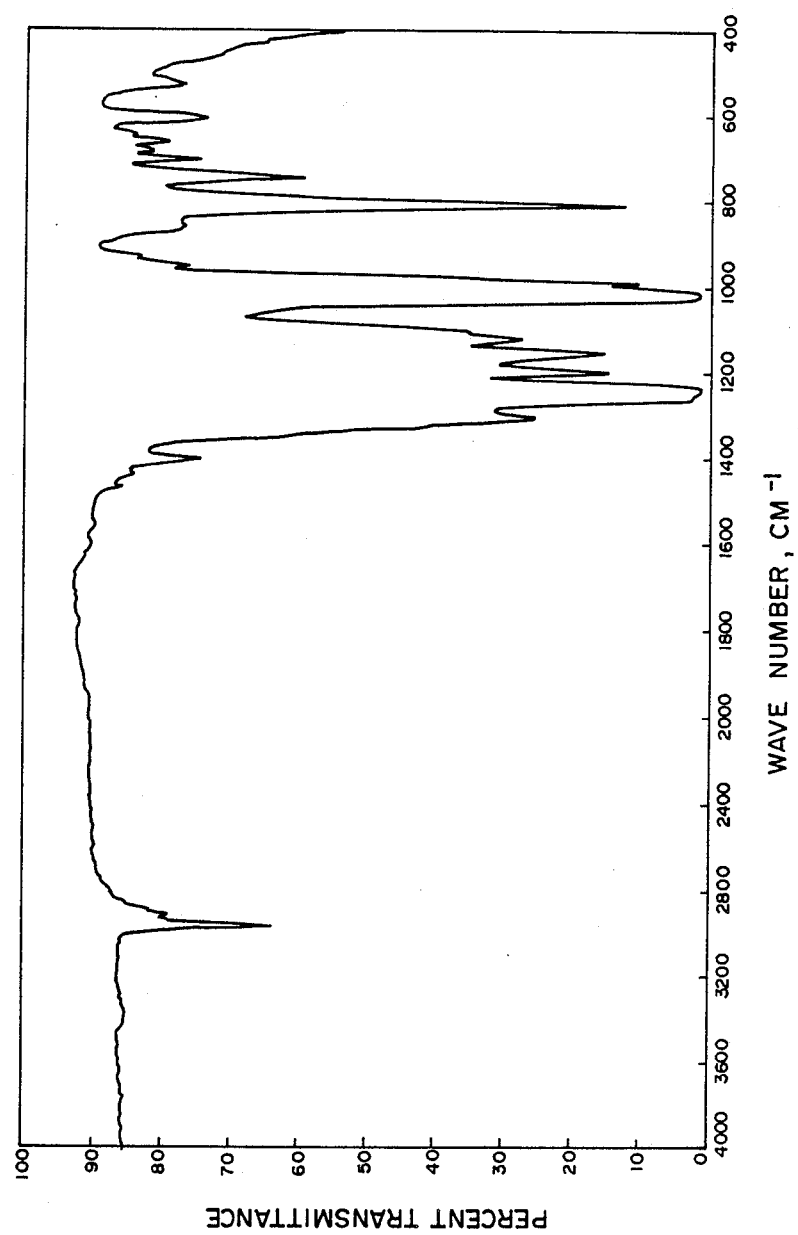
Figure 6:
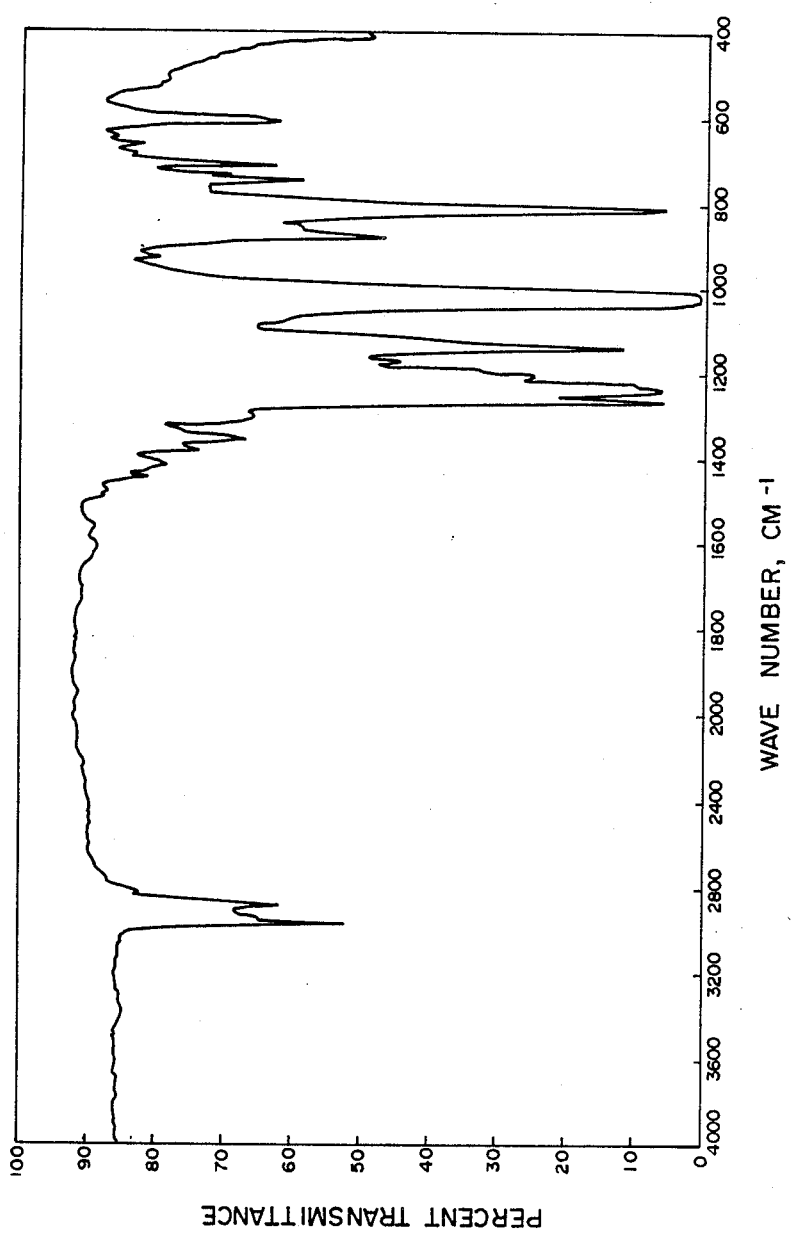
Figure 7:
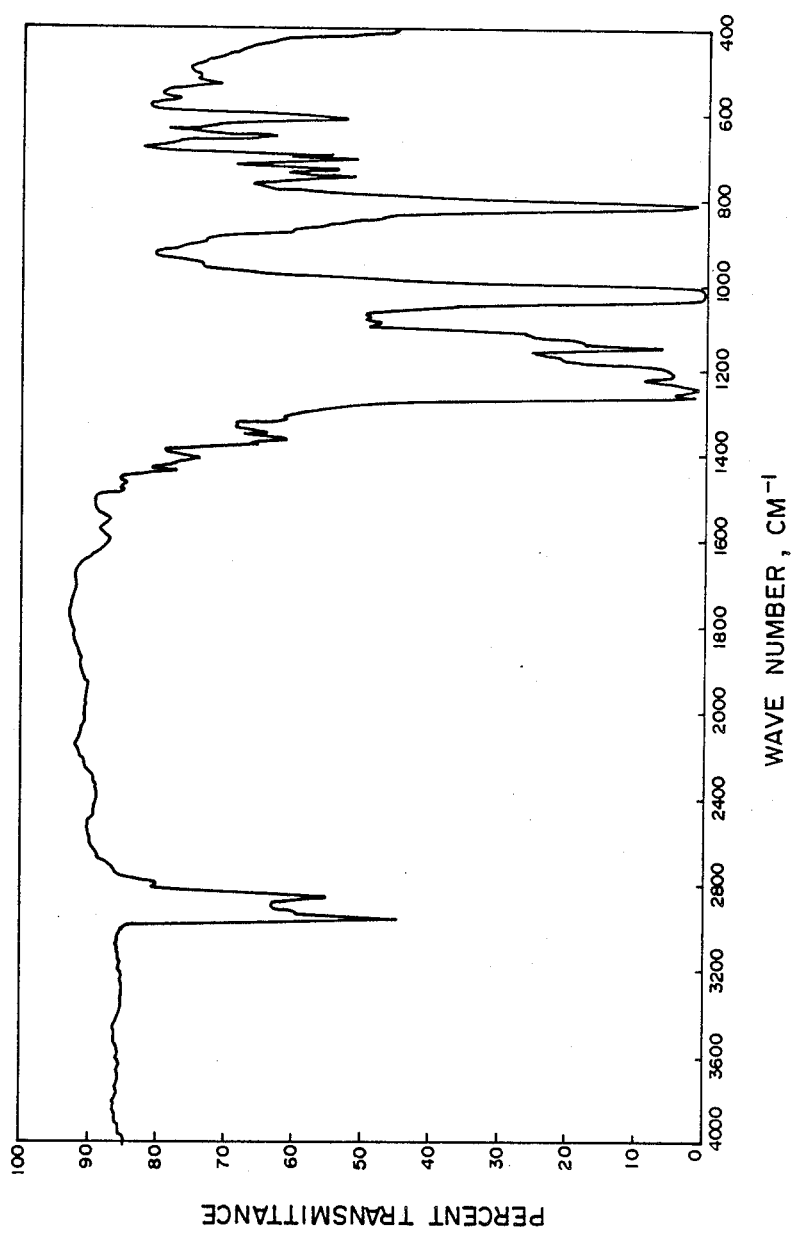
Figure 8:
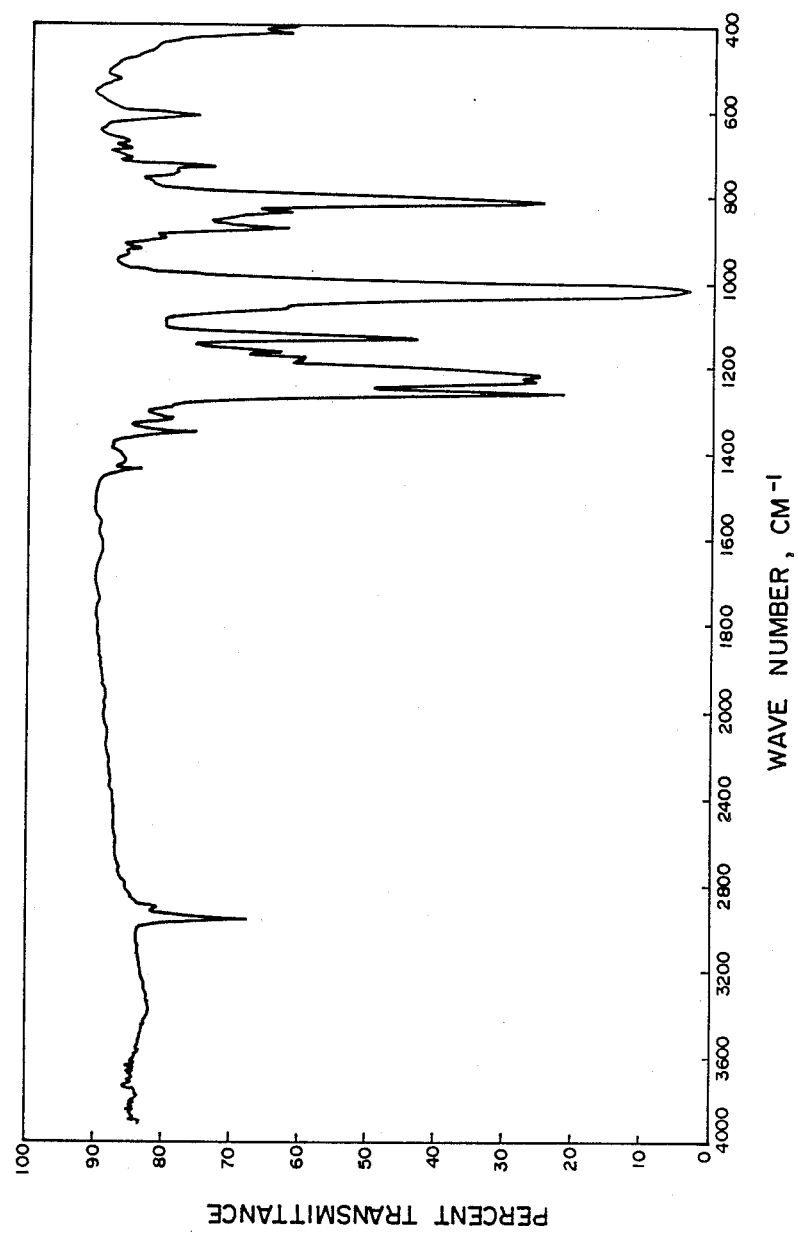
Figure 9:
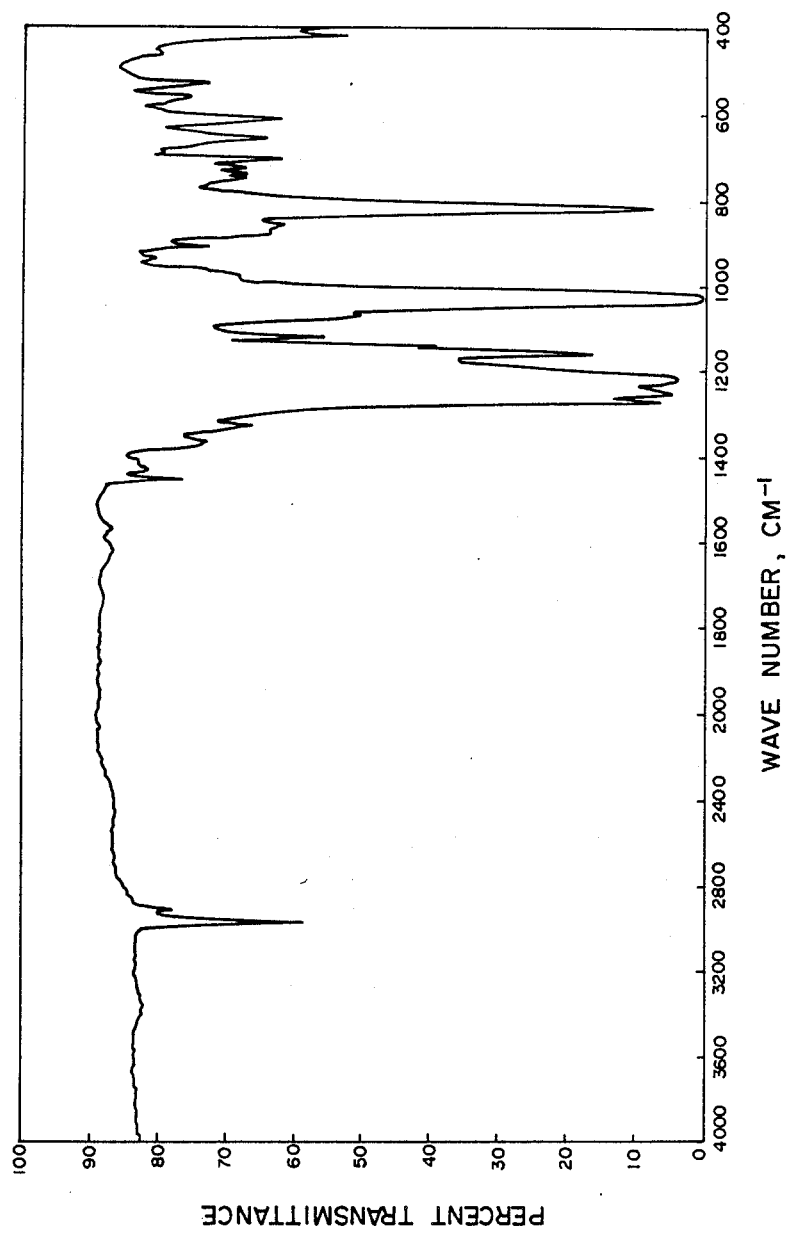

IR spectrum: As shown in FIG. 2.

Characteristic absorption (cm$^{-1}$): 1,020 (Si—O), 1,000–1,400 (C—F).

NMR spectrum: δ(ppm) (in CCl$_4$; internal standard: CHCl$_3$):
0.37–0.73 (m, 2H, Si—CH$_2$—C),
1.30–1.77 (m, 2H, C—CH$_2$—C),
2.07–2.83 (m, 2H, C—CH$_2$—CF),
3.23–3.83 (m, 4H, O—CH$_2$—O).

From the above results, the compound obtained was confirmed to be an organosilicon compound represented by the formula:

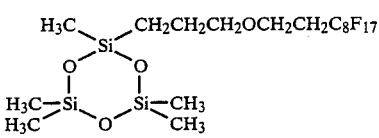

Yield: 71%.

Examples 3 to 9

Procedures taken in Example 1 were repeated to obtain a compound in each of Examples 3 to 9, except that dichlorosilane compounds shown in Table 1 were used in place of the dichlorosilane compound represented by formula (IV).

TABLE 1

| | Dichlorosilane compound |
|---|---|
| Example 3 | $\text{CH}_3\text{Si}(\text{CH}_2)_3\text{OCH}_2\text{CF}(\text{OCF}_2\text{CF})\text{F}$ with $\text{Cl}_2$ on Si, $\text{CF}_3$ $\text{CF}_3$ |
| Example 4 | $\text{CH}_3\text{Si}(\text{CH}_2)_3\text{OCH}_2\text{CF}(\text{OCF}_2\text{CF})_3\text{F}$ with $\text{Cl}_2$, $\text{CF}_3$ $\text{CF}_3$ |
| Example 5 | $\text{CH}_3\text{Si}(\text{CH}_2)_3\text{OCF}_2\text{CF}(\text{OCF}_2\text{CF})_2\text{F}$ with $\text{Cl}_2$, $\text{CF}_3$ $\text{CF}_3$ |
| Example 6 | $\text{CH}_3\text{Si}(\text{CH}_2)_3\text{O}(\text{CH}_2)_2\text{C}_4\text{F}_9$ with $\text{Cl}_2$ |
| Example 7 | $\text{CH}_3\text{Si}(\text{CH}_2)_3\text{O}(\text{CH}_2)_2\text{C}_6\text{F}_{13}$ with $\text{Cl}_2$ |
| Example 8 | $\text{CH}_3\text{SiCH}_2\text{CH}_2\text{C}_4\text{F}_9$ with $\text{Cl}_2$ |
| Example 9 | $\text{CH}_3\text{SiCH}_2\text{CH}_2\text{C}_8\text{F}_{17}$ with $\text{Cl}_2$ |

The compounds obtained were subjected to elemental analyses and also to measurement of IR spectra and NMR spectra to obtain the results shown in Table 2, Table 3 and FIGS. 3 to 9 (IR spectra). As to the characteristic absorption in IR spectra, a peak based on the Si—O bond was seen at 1,020 cm$^{-1}$, and a broad peak based on the C—F bond, at 1,000 to 1,400 cm$^{-1}$.

TABLE 2

| | (Results of elemental analyses) | | | |
|---|---|---|---|---|
| Example | C | H | F | Si |
| 3 Calculated*: | 29.78 | 4.11 | 37.02 | 14.92 |
| Found: | 29.75 | 4.09 | 37.05 | 14.96 |
| (*as $C_{14}H_{23}O_5F_{11}Si_3$) | | | | |
| 4 Calculated*: | 26.79 | 2.59 | 48.73 | 9.40 |
| Found: | 26.76 | 2.58 | 48.76 | 9.43 |
| (*as $C_{20}H_{23}O_7F_{23}Si_3$) | | | | |
| 5 Calculated*: | 26.64 | 2.76 | 47.09 | 10.99 |
| Found: | 26.62 | 2.74 | 47.12 | 10.96 |
| (*as $C_{17}H_{21}O_6F_{19}Si_3$) | | | | |
| 6 Calculated*: | 32.80 | 4.92 | 33.36 | 16.44 |
| Found: | 32.84 | 4.95 | 33.35 | 16.46 |

TABLE 2-continued

| | (Results of elemental analyses) | | | |
|---|---|---|---|---|
| Example | C | H | F | Si |
| (*as $C_{14}H_{25}O_4F_9Si_3$) | | | | |
| 7 Calculated*: | 31.37 | 4.11 | 40.32 | 13.75 |
| Found: | 31.36 | 4.12 | 40.35 | 13.77 |
| (*as $C_{16}H_{25}O_4F_{13}Si_3$) | | | | |
| 8 Calculated*: | 29.07 | 4.21 | 37.62 | 18.54 |
| Found: | 29.09 | 4.21 | 37.65 | 18.56 |
| (*as $C_{11}H_{19}O_3F_9Si_3$) | | | | |
| 9 Calculated*: | 27.53 | 2.93 | 49.34 | 12.87 |
| Found: | 27.56 | 2.95 | 49.37 | 12.86 |
| (*as $C_{15}H_{19}O_3F_{17}Si_3$) | | | | |

TABLE 3

| | (NMR spectra) | | | |
|---|---|---|---|---|
| Example | | | Data | |
| 3 | 0.37–0.75 | m | 2H | Si—CH$_2$—C |
| | 1.37–1.93 | m | 2H | C—CH$_2$—C |
| | 3.35–3.65 | t | 2H | C—CH$_2$—O |
| | 3.75–4.10 | d | 2H | O—CH$_2$—CF |
| 4 | 0.37–0.76 | m | 2H | Si—CH$_2$—C |
| | 1.37–1.93 | m | 2H | C—CH$_2$—C |
| | 3.34–3.65 | t | 2H | C—CH$_2$—O |
| | 3.73–4.10 | d | 2H | O—CH$_2$—CF |
| 5 | 0.35–0.80 | m | 2H | Si—CH$_2$—C |
| | 1.58–1.97 | m | 2H | C—CH$_2$—C |
| | 3.81–4.11 | t | 2H | C—CH$_2$—O |
| 6 | 0.35–0.73 | m | 2H | Si—CH$_2$—C |
| | 1.30–1.80 | m | 2H | C—CH$_2$—C |
| | 2.13–2.82 | m | 2H | C—CH$_2$—CF |
| | 3.20–3.80 | m | 4H | C—CH$_2$—O |
| 7 | 0.35–0.75 | m | 2H | Si—CH$_2$—C |
| | 1.33–1.85 | m | 2H | C—CH$_2$—C |
| | 2.08–2.83 | m | 2H | C—CH$_2$—CF |
| | 3.22–3.82 | m | 4H | C—CH$_2$—O |
| 8 | 0.59–1.01 | m | 2H | Si—CH$_2$—C |
| | 1.56–2.51 | m | 2H | C—CH$_2$—CF |
| 9 | 0.58–1.00 | m | 2H | Si—CH$_2$—C |
| | 1.57–2.50 | m | 2H | C—CH$_2$—CF |

From the above results, the compounds obtained were comfirmed to be organisilicon compounds represented by the formula:

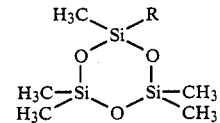

Here, R is as shown in Table 4 below.

TABLE 4

| Example | R |
|---|---|
| 3 | —(CH$_2$)$_3$OCH$_2$CF(OCF$_2$CF)F with CF$_3$, CF$_3$ |
| 4 | —(CH$_2$)$_3$OCH$_2$CF(OCF$_2$CF)$_3$F with CF$_3$, CF$_3$ |
| 5 | —(CH$_2$)$_3$OCF$_2$CF(OCF$_2$CF)$_2$F with CF$_3$, CF$_3$ |
| 6 | —(CH$_2$)$_3$O(CH$_2$)$_2$C$_4$F$_9$ |
| 7 | —(CH$_2$)$_3$O(CH$_2$)$_2$C$_6$F$_{13}$ |
| 8 | —CH$_2$CH$_2$C$_4$F$_9$ |
| 9 | —CH$_2$CH$_2$C$_8$F$_{17}$ |

What is claimed is:

1. An organosilicon compound represented by general formula (I):

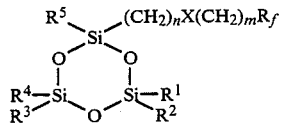 (I)

wherein $R^1$, $R^2$, $R^3$, $R^4$ and $R^5$ may be the same or different and each represent an alkyl group having 1 to 4 carbon atoms; $R_f$ represents

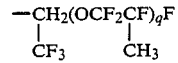

where q represents an integer of 1 to 5, or

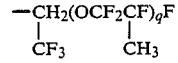

where q is as defined above; and X represents —O— or —CH$_2$—; provided that n is 3 and m is an integer of 0 to 2 when X represents —O—, and n is 0 and m is 1 when X represents —CH$_2$—.

2. The compound of claim 1, wherein $R^1$, $R^2$, $R^3$, $R^4$ and $R^5$ each represent a methyl group.

* * * * *